United States Patent [19]

Shalaby et al.

[11] Patent Number: 4,461,298

[45] Date of Patent: Jul. 24, 1984

[54] COMPOSITE SUTURES OF SILK AND HYDROPHOBIC THERMOPLASTIC ELASTOMERS

[75] Inventors: Shalaby W. Shalaby, Lebanon, N.J.; Martin Stephenson; Louise Schaap, both of Peterborough, Canada; Graham H. Hartley, deceased, late of Peterborough, Canada, By Marilyn Hartley, personal representative

[73] Assignee: Ethicon, Inc., Somerville, N.J.

[21] Appl. No.: 401,661

[22] Filed: Jul. 26, 1982

[51] Int. Cl.$^3$ .............................................. A61L 17/00
[52] U.S. Cl. .................................... 128/335.5; 528/296
[58] Field of Search ................ 128/335.5, 334 R, 1 R; 427/2; 528/296–297, 301–302

[56] References Cited

U.S. PATENT DOCUMENTS

| | | | |
|---|---|---|---|
| 2,751,910 | 6/1956 | Howes | 427/2 |
| 3,187,752 | 6/1965 | Glick | 128/335.5 |
| 3,297,033 | 1/1967 | Schmitt et al. | 128/335.5 |
| 3,307,971 | 3/1967 | Kurtz | 128/335.5 |
| 3,322,125 | 5/1967 | Kurtz | 128/335.5 |
| 3,424,164 | 1/1969 | Block | 427/2 |
| 3,527,556 | 9/1970 | Riley | 128/335.5 |
| 3,527,650 | 9/1970 | Block | 117/7 |
| 3,576,773 | 4/1971 | Vaginay | 528/296 |
| 3,665,927 | 5/1972 | Kurtz | 128/335.5 |
| 3,700,489 | 10/1972 | Borysko | 427/2 |
| 3,942,532 | 3/1976 | Hunter et al. | 128/335.5 |
| 4,043,344 | 8/1977 | Landi et al. | 128/335.5 |
| 4,105,034 | 8/1978 | Shalaby et al. | 128/335.5 |
| 4,185,637 | 1/1980 | Mattei | 128/335.5 |
| 4,209,607 | 6/1980 | Shalaby et al. | 128/335.5 |
| 4,246,904 | 1/1981 | Kaplan | 128/335.5 |
| 4,314,561 | 2/1982 | Kaplan | 128/335.5 |
| 4,349,469 | 9/1982 | Davis et al. | 528/296 |
| 4,388,926 | 6/1983 | Shalaby et al. | 128/335.5 |

FOREIGN PATENT DOCUMENTS 902439  6/1972  Canada ............................. 117/183

OTHER PUBLICATIONS

PTO Scientific Lib. Computer Search, (9 pages).

*Primary Examiner*—C. Fred Rosenbaum
*Assistant Examiner*—Gene B. Kartchner
*Attorney, Agent, or Firm*—Leonard Kean

[57] ABSTRACT

Composite suture of multifilament silk embedded in a highly flexible, hydrophobic highly deformable matrix made of thermoplastic elastomer. This suture exhibits minimal irritation to living tissue and retains its strength in vivo for extended periods of time and also retains the desirable handling qualities of silk. The suture is prepared by treating a multifilament silk suture with a solution of a suitable polymer in a solvent and heating the moving suture to obtain a continuous impregnation of the silk with the elastomer.

14 Claims, No Drawings

COMPOSITE SUTURES OF SILK AND HYDROPHOBIC THERMOPLASTIC ELASTOMERS

BACKGROUND OF THE INVENTION

This invention relates to a non-irritating composite suture of silk and hydrophobic thermoplastic elastomers containing at least 25% soft segments which composite suture retains the handling qualities of silk and is also capable of retaining at least thirty-two percent of its initial mechanical strength in vivo after eight weeks. This composite suture has surface barrier properties of a monofilament and tissue reaction comparable to common synthetic sutures. This invention also relates to the process for preparing the composite suture.

Many natural and synthetic materials are presently used as surgical sutures. These materials may be used as single filament strands, i.e., monofilament sutures, or as multifilament strands in a braided, twisted or other multifilament construction. Silk does not lend itself to the fabrication of monofilament sutures and is accordingly generally used in one of the multifilament constructions, preferably the braided form. This results in a silk suture having desirable handling characteristics, being sufficiently flexible and having good knot-tying ability and knot security. However, presently available untreated silk sutures are known (a) to provoke a significant tissue reaction in the biologic environment, (b) have a significant strength loss in living tissues (typically a 2-0 silk suture retains about twenty percent of its original strength after eight weeks, post-implantation, and (c) to lack the surface barrier properties needed for retarding cellular infiltration into the suture interior in living tissue.

The composite suture of the present invention displays equivalent handling properties to those of the untreated braided silk suture, it elicits reduced tissue reaction after seven days and later post-implantation intervals, and when implanted intramuscularly, is more effective in retarding cellular infiltration due to the monofilamentous geometry of the composite suture and it is characterized by improved strength retention after fifty-six days post-implantation.

The prior art discloses a number of methods for coating sutures in general. Coating material for sutures normally would require low surface friction characteristics so as to facilitate the knot-tying ability of the resultant coated suture. Contrary to such expectations, the present invention utilizes an elastomer (which has high surface friction characteristics) in preparing the present composite suture.

Braided silk sutures are desirably flexible due to the interlocking geometry of the fibers. in accordance with the present invention, a multifilament silk suture is treated with a hydrophobic, limp thermoplastic elastomer in order, not only to coat the suture, but to substantially fill all the interstices between the silk filaments. It has been found, surprisingly, that the particular elastomers utilized in accordance with the present invention, when filling the spaces between the silk fibers, do not adversely affect the flexibility of the suture as a whole.

DESCRIPTION OF THE PRIOR ART

U.S. Pat. No. 3,527,650 teaches that multifilament non-absorbable sutures can be improved with respect to tie-down performance by depositing solid particles of polytetrafluoroethylene and a binder resin on the *external surface*. No infiltration of this coating to the suture interior was described in this patent. Furthermore, the coating flakes off during use, especially during knot tie-down.

According to U.S. Pat. No. 3,942,532, non-absorbable sutures can be improved with respect to tie-down performance by coating them with a linear polyester having a molecular weight between about 1,000 and about 15,000 and at least two carbon atoms between the ester linkages.

This patent pertains to simple linear thermoplastic polyesters which are highly crystalline, low melting materials. These are expected to impart lubricity and are not (a) segmented in structure, (b) elastomeric or (c) significantly capable of contributing to the mechanical properties of braided sutures (including silk) to any discernible extent.

U.S. Pat. No. 3,297,033 discloses that synthetic absorbable sutures can be coated with coating materials used on conventional sutures, such as a silicone or beeswax to modify handling. However, it does not describe any material or system that can be combined with braided silk sutures to form the unique composite sutures subject of the present invention.

U.S. Pat. No. 4,043,344 shows that the handling characteristics and particularly the knot run down and tissue drag characteristics of non-absorbable sutures are improved by a coating with a lubricating film of bioabsorbable copolymer having copolyoxyethylene blocks and polyoxypropylene blocks. The copolymer has a molecular weight such that it is pasty to solid at 25° C. This lubricant coating is described as absorbable (in vivo) in less than two days which results in improved long term knot security.

The lubricant coating as described should (a) have a low molecular weight, about 8350 Dalton, and low Tm and hence would be expected to have hardly any integrity at usual levels of stress; (b) it is soluble in the biologic environment and likely to migrate to the surrounding tissue in two days to cause additional foreign body reaction; (c) it is water-soluble and hence would be expected to provide minimum lubricity during wet tie-down and (d) would not be expected to render a commercial silk suture less irritating to tissue and more resistant towards losing its breaking strength, for the coating does not act as a hydrophobic inert barrier about the braid components and does not mask effectively the undesirable morphological features of a braided suture.

U.S. Pat. No. 4,185,637 discloses a multifilament suture having improved tie-down properties, said suture being coated with from about 1 to 5 percent by weight of the dry residue of a composition comprising a gel of a polyvalent metal ion salt of $C_6$ or higher fatty acid in a volatile organic solvent.

The coating described by this patent can only serve as a lubricant, for it is a low molecular weight system that cannot impart any discernible physical changes to the mechanical integrity of the suture braid construction. If used for silk sutures, this absorbable coating would not be expected to decrease the tissue reaction or increase the strength retention.

According to U.S. Pat. No. 4,105,034 the tie-down properties of a multifilament surgical suture are improved by coating the suture with an absorbable composition comprising a low molecular weight polyalkylene oxalate.

If silk sutures were to be treated with such a coating, the latter would be expected to only impart desirable surface lubricity, without affecting the tissue reaction or breaking strength retention of the implanted suture in any positive sense. This is simply because the coating is an absorbable low molecular weight material which limits the residence time about the fibers and the effect on the suture properties of the braid.

Canadian Pat. No. 902439 describes a polyfilamentary silk suture having a plurality of fine solid particles of insoluble synthetic polymeric material incorporated in the interstices thereof, in an amount sufficient to embue the suture with substantially the properties of a monofilament. However, these particles cannot be expected to act as a hydrophobic inert barrier about the braid components and accordingly, the method of said reference is not likely to increase the tissue reaction or increase the strength retention of the suture.

In view of the above discussion it will be seen, with respect to non-absorbable sutures such as braided silk sutures, that the prior art does not disclose any effective method for reducing tissue reaction at later post-implantation periods, retarding cellular infiltration or bringing about improved strength retention after eight weeks post-implantation. It is accordingly an object of the present invention to prepare a composite suture which is non-irritating and retains the handling qualities of silk, and which is capable of retaining a higher proportion of the initial mechanical strength, in vivo, after eight weeks, than in the case of an untreated silk suture per se. It is a further object of the present invention to provide a composite suture having surface barrier properties comparable to those of a monofilament and tissue reaction comparable to common synthetic sutures. It is a further object of the invention to provide a composite silk-elastomer suture in which the elastomer substantially fills all the interstices between the silk filaments and having properties such that the elastomer nevertheless permits the individual components of the silk to flex in such a way that the flexibility of the silk suture, as a whole, is not impaired. It is yet a further object of the present invention to provide a composite silk-elastomer suture wherein the primary strength is provided by the silk (since the elastomer matrix is much less strong).

SUMMARY OF THE INVENTION

In accordance with the present invention there is provided a non-irritating composite suture retaining the handling qualities of silk, which, in the case of size 5-0, is capable of retaining at least 32% of its initial mechanical strength, in vivo, after eight weeks; said suture having surface barrier properties against cell infiltration comparable to those of a monofilament and tissue reaction comparable to common synthetic sutures; comprising multifilament silk embedded in a hydrophobic, limp thermoplastic elastomer; said elastomer comprising copolymers having hard and soft components, said soft components comprising about 25–80% by weight of said elastomer, depending upon the melting temperature and crystallizability of the hard components, said elastomer having a suitable molecular weight sufficient to provide a solution viscosity that is consistent with optimum diffusion into the interior of the suture structure, resulting in a high integrity matrix which does not flake when the suture is subjected to mechanical stress.

In accordance with the preferred embodiment of the present invention, the silk is of braided construction and the elastomer is selected from the group consisting of copolymers having the following recurring units:

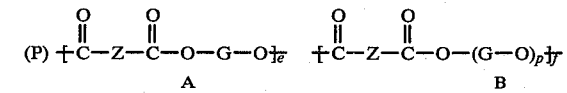

wherein each G individually represents an alkylene group of from 2 to 6 carbon atoms, and p is 9 to 15, e and f each represent a number having a value greater than 1 such that the B units comprise 50 to 80 weight percent of the copolymer and the A units comprise the remainder; wherein Z represents 1,4-phenylene, 1,3-phenylene or trans-1,4-cyclohexylene;

(Q) a copolymer consisting essentially of a multiplicity of recurring A [poly(alkylene terephthalate, isophthalate or cyclohexane-1,4-dicarboxylate)] and B [poly(alkylene dimerate)] units having the following general formula:

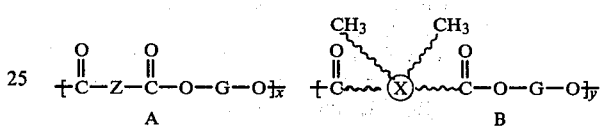

wherein x and y are integers, such that the B units comprise 50 to 80 weight percent of the copolymer, and the A units comprise the remainder;

denotes a branched hydrocarbon chain containing from 24 to 32 carbon atoms and Z and G are as hereinabove defined;

(R) a copolymer consisting essentially of a multiplicity of recurring poly(alkylene) terephthalate, isophthalate or cyclohexane-1,4-dicarboxylate, and poly(alkylene) alkyl or alkenyl succinate units having the following general formula:

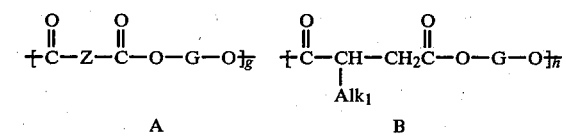

wherein $Alk_1$ is a linear or branched alkyl or alkenyl radical with a chain length of about 4 to 30 carbon atoms and g and h are integers such that the B units comprise 50 to 80 weight percent of the copolymer and the A units comprise the remainder; and Z and G are as hereinabove defined;

(S) a random copolymer having the following general formula:

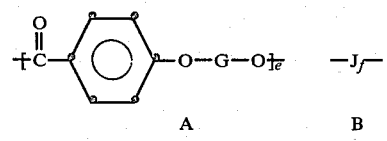

wherein J is either:

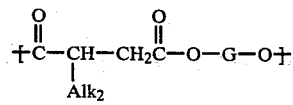   (1)

or

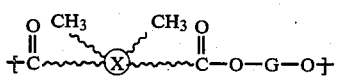   (2)

wherein Alk₂ is alkyl or alkenyl moieties with a chain length of 8 to 30 carbon atoms;

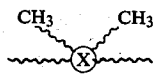

denotes a branched hydrocarbon chain with an estimated formula of $C_{32}H_{60}$, or

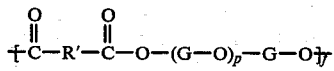   (3)

wherein p is 9 to 15 and G is as hereinabove defined and R' is an aliphatic or aromatic disubstituted moiety and wherein e and f are such that the B units comprise about 25 to 50% by weight of the copolyester and the A units comprise the remainder.

The elastomer of the present invention possesses an inherent viscosity which ranges between about 0.02 and 1.4, and has a melting temperature by thermal microscopy of between about 80° and 180° C. The elastomer comprises between 5 and 50% by weight of the total composite system and preferably has a molecular weight of at least 2000 Dalton, and most preferably at least 10,000 Dalton. Preferably the soft segments of the elastomer of the formulae (P), (Q) and (R) comprise between 55% and 75% by weight thereof and in the instance wherein the elastomer has the above formulae (P), (Q), or (R), the soft segments comprise between 60 and 70% thereof. Furthermore, in the instance wherein the elastomer has the formula (S), the soft segments preferably comprise between 30 and 50% thereof.

In the instance wherein the elastomer has the formula (P), the inherent viscosity in HFIP (hexafluoro-2-propanol) is preferably between 0.8 and 1.3. In the instance wherein the elastomer has the formula (Q) or (R), the inherent viscosity in hexafluoro-2-propanol is preferably between 0.2 and 0.7; and in the instance wherein the elastomer has the formula (S) the inherent viscosity in hexafluoro-2-propanol is preferably between 0.3 and 0.6.

Within the scope of the present invention is a composite suture, having a surgical needle attached to at least one end, preferably in a sterile condition.

In this connection, it is important that sutures be presented to the operating room in sterile condition. Several methods of achieving sterility are known. Of these the most commonly employed method for silk sutures consists of exposure to 2.5 Mrads of γ irradiation derived from a Cobalt 60 source. It is important therefore that the thermoplastic elastomers used in this invention be capable of resisting exposure to this level of irradiation without significant change in their physical properties.

In accordance with the present invention, there is also provided a method of preparing a non-irritating and strength retaining composite silk thermoplastic elastomer suture comprising the steps of (a) treating a multifilament silk suture with a hydrophobic, limp thermoplastic elastomer dissolved in a solvent therefor at a temperature between 20° and 80° C. but preferably between 30° and 50° C. in order to coat said suture, said elastomer comprising copolymers having hard and soft components, said soft components comprising about 25-80% by weight of said polymer; said elastomer having a suitable molecular weight sufficient to provide a solution viscosity that is consistent with optimum diffusion into the interior of the suture structure, resulting in a high integrity matrix which does not flake when the suture is subjected to mechanical stress; and optionally, (b) rapidly heating the treated suture at a temperature between about 340° and 500° C. to obtain a continuous and consistent impregnation of the multifilament silk suture, and to substantially fill all the interstices between the silk filaments.

DESCRIPTION OF PREFERRED EMBODIMENTS

The preferred synthetic matrix (P), used to prepare the composite suture of the present invention, is a segmented polyether-ester made by the condensation of dimethyl terephthalate, polyoxytetramethylenediol (molecular weight 650 to 10,000 Dalton and preferably 1000 Dalton) and butanediol in the presence of a typical polyesterification catalyst [e.g. Ti(OBu)₄, Ti(OBu)₄+Mg(OAc)₂], optionally, an antioxidant of the hindered phenol type (e.g. Irganox 1098 [N,N'-hexamethylene bis (3,5-ditert-butyl-4-hydroxyhydrocinnamide] at 0.1 to 1%) or aromatic secondary amine type (e.g. Naugard 445 [4,4'bis(α,α-dimethylbenzyl)-diphenylamine] at 0.2 to 1%). The polymerization can be achieved under conventional conditions of temperature, pressure and stirring. The resulting polymer is characterized by having long sequences of crystallizable polybutylene terephthalate (4GT) units linked to low Tm or liquid (at room temperature) poly(polyoxytetramethylene) terephthalate (POTMT); these units are commonly referred to as hard and soft segments, respectively. The structure of the matrix material can be represented as follows:

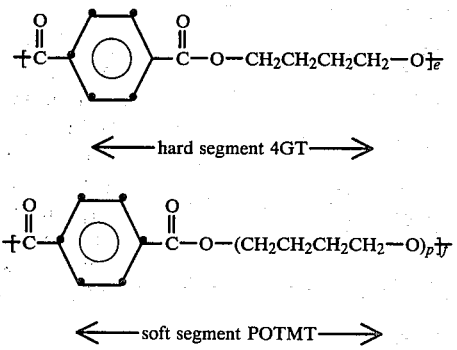

Although some of these segmented copolyesters are availble commercially and disclosed broadly in U.S. Pat. No. 3,023,192 (sold in the U.S. under the trade name Hytrel) the relatively high proportion of hard segments and high molecular weight of the commercially available products render them less suitable for use in the present invention, and accordingly special compositions are made in order to provide optimum matrixes for the composite sutures of this invention. The composition and physical properties of two typical matrix materials are shown in Table I. If tested in the appropriate physical form (e.g. compression molded film Die C) these polymers are expected* to have an ultimate elongation of 300%, ultimate tensile strength of 5000 psi and a flex. modulus of <10,000 psi.

*See A. Lilconitkul & S. L. Cooper, Rubber Chem. Tech. 50 (1), 1 (1977) and references therein.

TABLE 1

| Properties of Two Typical Matrix Materials | | |
|---|---|---|
| Polymer No.: | 135 | 137 |
| Soft Segment Content Wt. % (determined by NMR) | 63 | 71 |
| Inherent Viscosity in HFIP (hexafluoro-2-propanol) | 1.27 | 1.12 |
| Melting Temperature by Microscopy | 126–143 | 138–145° C. |
| % Crystallinity, by X-ray | — | 15–20 |

Based on available physical data* on compositions other than those described in Table I, the glass transition temperature of polymers #135 and 137 are expected to be well below −40° C. irrespective of the analytical procedure used for the Tg measurement.

The crystallinity detected in sample #137 is shown to be due to the hard 4GT segments. Considering the available data on Hytrel-type polymers* the molecular weight of polymers #135 and 137 can be equal to or exceed 10,000 Dalton.

The synthetic matrix Q) is prepared by the polycondensation of dimethyl terephthalate, dimer acid, or preferably its diisopropyl ester and a polymethylene diol (n=4 to 8, and preferably 4).

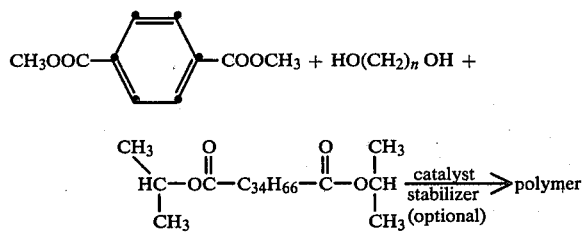

The preferred parent dimer acid of the diisopropyl ester utilized in the polymerizations is derived from high purity oleic acid and is formed by a clay catalyzed high pressure dimerization of the oleic acid in the presence of water. The mechanism of formation of the dimer acid is probably free radical in nature and the product is believed to consist of a mixture of acyclic unsaturated $C_{36}$ acids. The unsaturated materials are then hydrogenated and the dimer ester used in the present polymerization possesses a slight degree of unsaturation as evidenced by an Iodine number of 5. In addition to the $C_{36}$ acids that make up the dimer acid there is present some monofunctional acid (iso-stearic) and a certain quantity of trifunctionality in terms of a "Trimer ($C_{54}$) acid." The former may act as a chain terminator and the latter as crosslinking agent. Detailed structures of the $C_{36}$ components of the dimer acid have not been elucidated as yet and the diacid is sometimes represented graphically as shown below (with four almost equal branches).

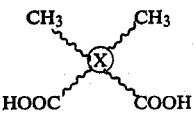

The reaction may be run in the absence or preferably in the presence of stabilizers taken from the types of hindered phenols or secondary aromatic amines. An example of the former is Irganox 1098 sold by Ciba-Geigy [N,N'-hexamethylene bis (3,5-ditert-butyl-4-hydroxy hydrocinnamide)] and an example of the latter is Naugard 445 sold by Uniroyal [4,4'-bis(α,α-dimethyl-benzyl)diphenyl amine)]. Oxides and alkoxides of numerous polyvalent metals may be employed as catalysts. A preferred catalyst for the polymerization is a mixture of about 0.1% tetrabutyl orthotitanate and about 0.005% magnesium acetate (percentages based on total charge weight).

The polymerization is run in two stages. In the first stage, run under nitrogen at temperatures ranging from 160° to 250° C., polycondensation via transesterification and esterification occurs resulting in oligomeric chains. These are converted to materials having high degree of polymerization in the subsequent step run at 240° to 255° C., at pressures of less than 1 mm of mercury.

The resulting polymers exhibit inherent viscosities (measured in hexafluoroisopropyl alcohol) of 0.5 to 0.9. The Tm of the polymers, depending on composition, varies from 100° to 180° C.

Polymerization Procedure for Preparing Matrix Q

For each mole of the desired amounts of dimethyl terephthalate and diisopropyl dimerate (obtained from Emery Industries as Emerest 2349), a 1.3 to 2.2 molar excess of a polymethylene diol and a given stabilizer are placed under nitrogen into a dry reactor fitted with an efficient mechanical stirrer, a gas inlet tube and a takeoff head for distillation. The system is heated under nitrogen to 160° C. and stirring is begun. To the homogeneous stirred solution the required amount of catalyst is added. The mixture is stirred and heated under nitrogen for given time periods of 190° C. (2–4 hours) and 220° C. (1–3 hours). The temperature is subsequently raised to 250° to 255° C. and over a period of 0.4–0.7 hours, the pressure is reduced in the system to below 1 mm/Hg (preferably in the range of 0.05 mm to 0.1 mm). Stirring and heating under the above conditions is continued to the completion of the polymerization. The endpoint is determined by either (a) estimating visually the attainment of maximum melt viscosity, (b) measuring inherent viscosity or melt indices of samples removed from the reaction vessel at intermediate time periods, and (c) using a calibrated torquemeter immersed into the mixture. In practice, depending on the terephthalate/dimerate ratio, in vacuo reaction times vary from 2 to 13 hours.

At the end of the polymerization cycle the hot mixture is equilibrated with nitrogen and allowed to cool slowly. The reaction product is isolated, chilled in liquid nitrogen and ground. The ground chips are dried at 80° to 110° C. for 8 to 16 hours under vacuum of 1 mm or less.

Copolyesters (Q) of aromatic diacids (e.g. terephthalic acid) and "dimer acids" of $C_{18}$ unsaturated fatty acids have been known for some time in the technical and patent literature.

Hoeschele [Angew.Makormol.Chem. 58/59, 229(1977)] disclosed the preparation of thermoplastic PBT (polybutylene terephthalate)/dimerate systems.

According to a number of patents [U.S. Pat. No. 3,390,108 (1968), U.S. Pat. No. 3,091,600 (1963) and British Pat. No. 994,441 (1965)], PET (polyethylene terephthalate) copolymers were disclosed containing small amounts of dimerate moieties.

In a few instances higher concentrations of dimerates are disclosed as being incorporated into PET copolymers [Belgium Pat. No. 649,158 (1964), U.S. Pat. No. 3,383,343 (1968) and French Pat. No. 1,398,551 (1965)]. Copolymer Q) is also disclosed in copending U.S. application Ser. No. 328,351.

The general structure of the poly[polymethylene terephthalate-co-(2-alkenyl or alkyl) succinate] R), useful in forming the composite sutures of the present invention, may be expressed as follows:

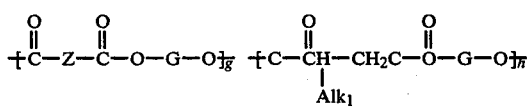

wherein Z and G are as defined hereinabove.

The structure belongs to the copolymer type and g and h can be predicted from the quantities of starting materials;

"G" is preferably 1,4-butylene, and

"Alk$_1$" is a linear or branched alkyl, or alkenyl (preferably a 2-alkenyl) group with a chain length of about 4 to 30 carbon atoms with the preferred range lying between about 12 and 22 carbon atoms.

The preferred polymers R) useful in the present invention are prepared by the polycondensation of dimethyl terephthalate, an alkyl (or 2-alkenyl) succinic anhydride and a polymethylene diol:

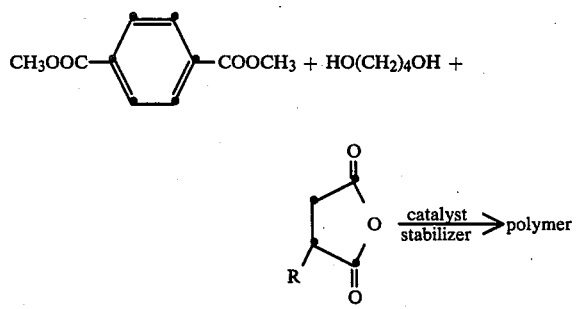

The required diols are commercially available. The substituted succinic anhydrides can be prepared by the "ene" reaction of maleic anhydride and an olefin (preferably a terminal olefin):

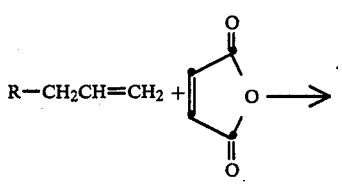

-continued

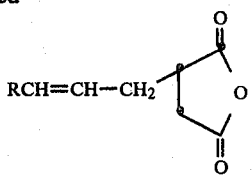

The reaction may be run in the absence or, preferably, in the presence of stabilizers such as hindered phenols, (e.g., Irganox 1098) or secondary aromatic amines, (e.g., Naugard 445). Acetates, oxides and alkoxides of numerous polyvalent metals may be employed as the catalyst such as, for example, zinc acetate, or magnesium acetate in combination with antimony oxide, or zinc acetate together with antimony acetate. However, the preferred catalyst for the polymerization is a mixture of about 0.1% (based on total charge weight) tetrabutyl orthotitanate and about 0.005% magnesium acetate.

The polymerization is run in two stages. In the first stage, run under nitrogen at temperatures ranging from 160° to 250° C., polycondensation via transesterification and esterification occurs, resulting in lower molecular weight polymers and oligomers. These are converted to higher molecular weight materials in the subsequent step run at 240° to 255° C., at pressures of less than 1 mm of mercury. The resulting polymers, exhibit inherent viscosities (measured in hexafluoroisopropyl alcohol) of 0.3 to 0.9. A representative molecular weight determination of one of the polymers by light scattering gives a value of $78 \times 10^3$ Daltons. The Tm of the polymers, depending on composition varies from about 100° to 180° C.

POLYMERIZATION PROCEDURE FOR PREPARATION OF POLYMER R

The desired amounts of dimethyl terephthalate, a 2-alkenyl succinic anhydride (or an alkylsuccinic anhydride), a 1.3 to 2.0 molar excess of a polymethylene diol and a given stabilizer are placed under nitrogen into a dry reactor fitted with an efficient mechanical stirrer, a gas inlet tube and a takeoff head for distillation. The system is heated under nitrogen to 160° C. and stirring is begun. To the homogeneous stirred reaction mixture the required amount of catalyst is added. The mixture is then stirred and heated under nitrogen for given time periods at 190° C. (2–4 hours) and 220° C. (1–3 hours). The temperature is subsequently raised to 250° to 255° C. and over a period of 0.4 to 0.7 hours, the pressure is reduced in the system to about 1 mm/Hg (preferably 0.05 mm to 0.1 mm). Stirring and heating under the above conditions is continued to complete the polymerization. The endpoint is determined by either (a) estimating visually the attainment of maximum belt viscosity, (b) measuring inherent viscosity or melt indices of samples removed from the reaction vessel at intermediate timer periods, or (c) using a calibrated torquemeter (attached to the stirrer of the reactor).

At the end of the polymerization cycle the molten polymer is extruded and pelletized (or slow cooled in the glass reactor, isolated and ground in a mill). The polymer is dried at 80° to 110° C. for 8–16 hours under reduced pressure. One alternate method of polymerization is set forth in U.S. Pat. No. 3,890,279.

Said U.S. Pat. No. 3,890,279 and U.S. Pat. No. 3,891,604 as well as copending U.S. application No.

218,998, disclose copolymer R). The flexible polyesters (S) useful in the present invention have rigid AB type ester units of an alkylene oxybenzoate and one of the following flexible AA-BB type ester sequences of (1) an alkylene, 2-alkenyl (or alkyl) succinate, (2) an alkylene dimerate (from a dimer of a long chain unsaturated fatty acid), (3) a dicarboxylate of poly(oxytetramethylene) glycol. Preferrred copolymers (S) have the following general formula:

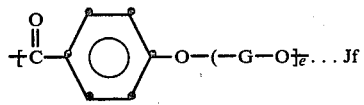

wherein G is defined hereinbefore and e and f can be determined by the amount of starting materials and J is either:

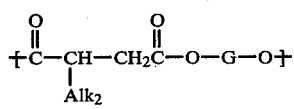 (1)

or

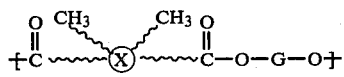 (2)

wherein Alk$_2$ is alkyl or alkenyl with a chain length of 8 to 30 carbon atoms;

denotes a branched hydrocarbon chain with an estimated formula of $C_{32}H_{60}$, or

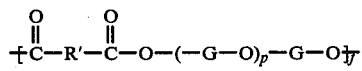 (3)

wherein R' is an aliphatic, cycloaliphatic or aromatic disubstituted moiety and p is about 10. The J units comprise about 25–50% by weight of the copolyester.

The general structures of the preferred copolymers (S) useful in the present invention may be expressed as follows:

I.
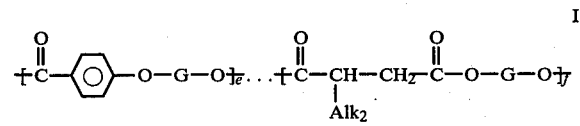

II.
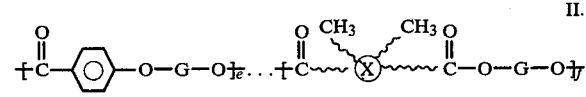

III.
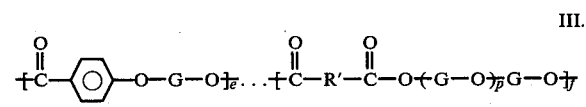

Copolymers (S) of type I are prepared typically by the polycondensation of p-(4-hydroxy-n-butoxy) benzoic acid (HB-OB) (or its methyl ester) (MB-OB), an alkenyl (or alkyl) succinic anhydride (or the corresponding dialkyl succinate) and a polymethylene diol in the presence of a suitable catalyst and preferably an antioxidant. Typical illustration of the reaction can be given as follows:

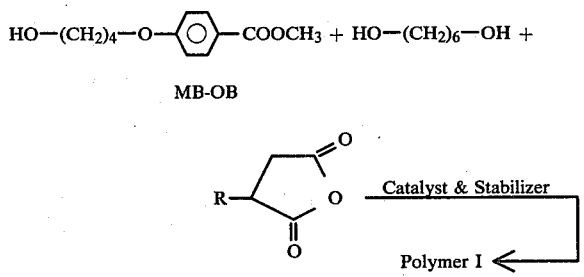

The MB-OB can be prepared according to the following tpical reaction scheme:

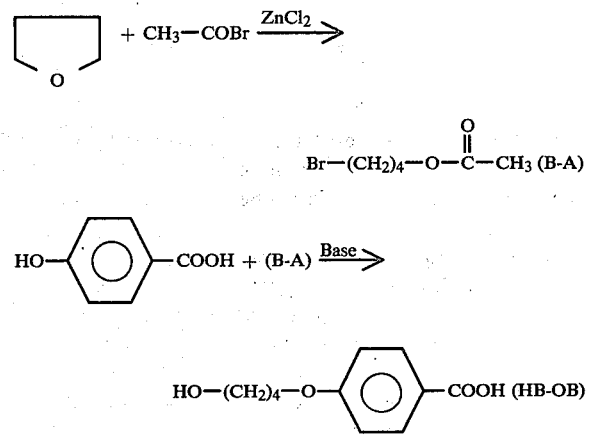

(HB-OB) + CH$_3$—OH $\xrightarrow{\text{Catalyst}}$ (MB-OB)

Copolymers (S) of type II are prepared typically by the polycondensation of p-(4-hydroxy-n-butoxy) benzoic acid (or its methyl ester), the dialkyl ester of dimer acid (or the free acid) and a polymethylene diol in the presence of a suitable catalyst and preferably an antioxidant. Typical illustration of the reaction can be given as follows:

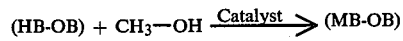
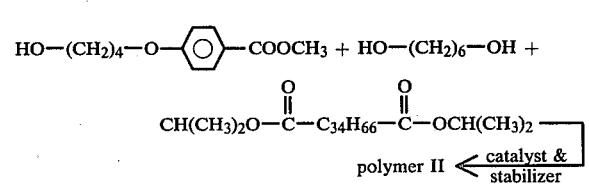

The parent dimer acid of the diisopropyl ester utilized in the polymerization is derived by a catalyzed high pressure dimerization of high purity oleic acid.

Copolymers (S) of type III are prepared typically by the polycondensation of p-(4-hydroxy-n-butoxy) benzoic acid (or its alkyl ester), dimethyl terephthalate, and polyoxybutylene diol (Mol. Wt. = 1000 Daltons), a suitable catalyst and stabilizer. Typical illustration of the reaction can be given as follows:

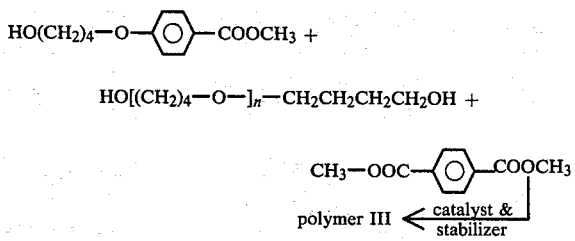

The polymerization may be conducted either in the absence or preferably in the presence of stabilizers of the hindered phenol or secondary aromatic amine type. An example of the former is Irganox 1098 and an example of the latter is Naugard 445. As catalyst, oxides and alkoxides of numerous polyvalent metals may be employed. However, the preferred polymerization catalysts are combinations of (a) tetrabutyl orthotitanate and/or magnesium acetate, (b) Mg(OAc)$_2$ and/or Sb$_2$O$_3$, and (c) combinations of tin and antimony catalysts, such as BuSnO (OH) and Sb$_2$O$_3$.

The polymerization is conducted in two stages. In the first stage, run under nitrogen at temperatures ranging from 160° to 250° C. polycondensation via transesterification and esterification occurs resulting in lower molecular weight polymers and oligomers. These are converted to higher molecular weight materials in the subsequent step run at 240° to 260° C., at pressures of less than 1 mm of mercury.

Polymerization Prodedure for Preparation of Polymer (S)

The desired amounts of monomers (and prepolymers as in system III) and a given stabilizer (optional) are placed under nitrogen into a dry reactor fitted with a mechanical stirrer, a gas inlet tube and a take-off head for distillation. The system is heated under nitrogen at 100° to 160° C. and stirring is begun. To the homogeneous stirred solution the required amount of catalyst is added. The mixture is then stirred and heated under nitrogen for given time periods at 190° C. (2–4 hours) and 220° C. (1–3 hours). The temperature is subsequently raised to 250° to 260° C. and over a period of 0.4–0.7 hours the pressure is reduced in the system to below 1 mm/Hg (preferably in the range of 0.05 mm to 0.1 mm). Stirring and heating under the above conditions is continued to the completion of the polymerization. The end point is determined by either (a) estimating visually the attainment of maximum melt viscosity, (b) measuring inherent viscosity or melt indices of samples removed from the reaction vessel at intermediate time periods, and (c) using a calibrated torquemeter immersed into the reaction mixture. In practice, depending on the copolymer composition, in vacuo reaction times varies from 2 to 8 hours.

At the end of the polymerization cycle the hot mixture is equilibrated with nitrogen and allowed to cool slowly. The reaction product is isolated, cooled in liquid nitrogen, and then ground. (In the case of metal reactors the hot melt is extruded at the bottom of the vessels into Teflon covered metal trays.) The ground chips are dried at 60° to 110° C. for 8–32 hours under a vacuum of 1 mm or less.

Copolymer (S) is disclosed in copending U.S. application Ser. No. 253,418.

In accordance with the present invention, pure silk filaments of braided construction are preferably used (a wide range of sizes being available). Addition of the elastomer to the silk does not significantly alter the diameter thereof. The elastomers utilized in accordance with the present invention are designed to be soft, ductile and elastomeric but capable of retaining their mechanical integrity under the ordinary mechanical stresses that the composite suture may be subjected to during end use. Retention of physical form and mechanical integrity is achieved by having quasi-crosslinks due to the crystallites of the crystaline phase in this system. This constitutes about 5 to 35% of the weight of the polymer. The low modulus and "soft handle" of the polymer are associated with the soft component of the polymer which comprises between about 25% and 80% by weight thereof [for polymers (P), (Q) and (R), the soft components comprise between 50% and 80% by weight thereof, preferably between 55% and 75%, and for polymer (S), the soft component comprises between 25% and 50%, preferably 30% to 50% by weight]. By virtue of their compositions, these quasi-crosslinked systems can be made to flow above the melting temperature (Tm) of the hard block. These thermal characteristics of the matrix material are of importance in connection with the optimal development of the composite suture, for it is then possible to rapidly sinter the matrix about the fibers of the silk braid at a temperature of above 200° C., without causing thermally induced degradation of the silk.

Suitable solvents for applying the elastomer matrix material to silk are halocarbons or mixtures of halo carbons with aromatics, methylene chloride being referred. Methylene chloride was selected for (a) its ability to induce certain amounts of swelling of the silk braid so as to ensure an ultimate strong joint between the braid components and the elastomeric matrix; (b) its ability to provide polymer solutions in a preferred case, with 20 to 5% concentrations having low Brookfield viscosities; this facilitates the impregnation of the braid with these solutions and (c) its high fugacity under mild devolatilization conditions, for drying the composite suture.

The elastomer is applied to the silk suture from a warm solution in a suitable solvent, as discussed above, especially dichloromethane. The temperature of the solution and the concentration of the polymer in the solution are not critical but it is preferred to have a temperature close to the boiling point of the solvent (about 40° C. in the case of dichloromethane) and a concentration which will not substantially increase the viscosity of the solution.

In order to carry out the process of the present invention, the braided silk suture is passed in a continuous process through a warm solution of elastomer, then immediately above the solution surface through a felt wipe, then vertically upward to air dry the treated suture over a short distance (e.g. 2 to 3 feet). The treated suture is then submitted to a rapid heating process in which the suture travels through a hot air zone to momentarily melt the elastomer layer inside the braided silk suture in order to substantially fill all interstices between the silk filaments. The temperature of the heated zone is adjusted for optimum polymer infiltration and depends upon the polymer used, the speed of the threadline and the suture diameter.

Typical temperatures of the hot air medium used for sintering during the rapid heat treatment range between 340° C. and 500° C. This temperature range is not necessarily the same as that of the suture itself. In the instance wherein the polymer has the structure (P) and the silk suture is size 2/0 travelling at 14 feet per minute, the temperature is preferably 415° C., the length of the heated zone being 22 centimeters.

The composite sutures of the present invention are extremely inert and have a minimal to very slight tissue reaction and are impervious to cellular ingrowth. They also exhibit a greater strength retention after eight weeks than silk coated with beeswax. These properties are demonstrated by the following studies:

In Vivo Performance of the Composite Suture

Needle Attachment and Sterilization

Needles are attached by hand swaging with a crimping tool and all samples are Cobalt sterilized.

In Vivo Implantation

Tissue Reactions of Polymer (P) Coated Silk Implanted in Rats

Materials
1. Materials of the following description are implanted, Polymer (P) being the product of Example 2:

| Sample No. | Size | Coating Treatment |
|---|---|---|
| 1 | 2-0 | Polymer (P) coating |
| 2 | 2-0 | Wax coated control |
| 3 | 5-0 | Polymer (P) coating |
| 4 | 5-0 | Wax coated control |

2. Amount of Material Required for Tissue Reaction Twenty-two needled strands at least eight inches long for each sample; strands are fitted with drilled straight tapered needles.
3. All samples are sterilized by Cobalt$^{60}$.

Procedures
1. Tissue Reaction Study
   A. Animals—Rats, female, Sprague Dawley, weight 150 to 200 grams. Thirty-six animals are used.
   B. Implantation Periods—7, 28 and 56 days.
   C. Experimental Design:
   Implantation of samples for tissue reaction are carried out according to the following design:

| Sample No. | Periods in Days/No. of Rats | | |
|---|---|---|---|
| | 7 | 28 | 56 |
| 1 | 3 | 3 | 3 |
| 2 | 3 | 3 | 3 |
| 3 | 3 | 3 | 3 |
| 4 | 3 | 3 | 3 |

D. Standard conditions of anesthesia and aseptic procedures are observed during suture preparation and surgical implantation.
   Utilizing one strand per side, 2 cm segments of each suture are implanted in the right and left gluteal muscles, two implants per side. Strands from the same suture sample are implanted on both sides of each rat.
   Rats are sacrificed according to experimental design after period of 7, 28, and 56 days. The gluteal muscles containing implants are excised and preserved in formalin fixative. A single block is cut transversely from each gluteal muscle and a single cross section of the two implant sites are stained with Hematoxylin and Eosin for microscopic evaluation. This procedure yields twelve sites per sample per period for evaluation.

E. Evaluation
1. Tissue Reaction Evaluation
A method modified from that described by Sewell, Wiland and Craver, (Surg., Gynecol. and Obstet. 100:483-494, 1955) is utilized to assess responses to implanted sutures. In this scheme the width of the reaction zone measured along the radius from the center of the suture cross section, is graded as:

| | Assigned Grade |
|---|---|
| 0-25 microns | 0.5 |
| 25-50 microns | 1.0 |
| 50-200 microns | 2.0 |
| 200-400 microns | 3.0 |
| 400-600 microns | 4.0 |

Cellular response is graded from 0 to 4 based on increasing concentrations of cells in the reaction zone. A grade of 0.5 is assigned where only a few cells are widely scattered in the reaction zone, while a grade of 4 is assigned where a high cellular concentration is present in the site.

Weighting factors are assigned to zone of reaction and inflammatory cells in computing reaction score as follows:

| Characteristic | Weighting Factor |
|---|---|
| Width of Zone | 5 |
| Overall cell density | 3 |
| Neutrophils | 6 |
| Giant cells | 2 |
| Lymphocytes/plasma cells | 1 |
| Macrophages | 1 |
| Eosinophils | 1 |
| Fibroblasts/fibrocytes | 1 |

A sample score is computed as follows:

| Parameter | Grade | × Weighting factor | = Score |
|---|---|---|---|
| Zone | 2 | 5 | 10 |
| Cell density | 2 | 3 | 6 |
| Macrophages | 2 | 1 | 2 |
| Giant cells | 1 | 2 | 2 |
| Fibroblasts | 2 | 1 | 2 |
| Total Score | | | 22 |

Adjectival ratings assigned to reaction scores are arbitrarily assigned within the following limits: 0—none; 1-8 minimal; 9-24 slight; 25-40 moderate; 41-56 marked; over 56, extensive.

2. Cellular Invasion of Strands
The extent of cellular invasion of suture fibrils is estimated subjectively as: none, minimal, slight, moderate or marked; these ratings correspond approximately to 0, 25, 50, 75 and 100 percent of suture invaded.

Determination of Tissue Reaction

The implants are recovered after the designated intervals and fixed in buffered formalin. Using standard histologic techniques, Hematoxylin and Eosin stained slides of the muscle cross-sections are prepared and examined microscopically, twelve sites per sample per period. Tissue reactions are evaluated according to the modified Sewell-Wiland method as described above (See Tables 2 and 3).

In addition, the muscle cross-sections containing the polymer (P) treated silk are stained with Oil Red 0 to visualize the presence of the polymer inside the silk braid.

Calculation of the tissue reaction area is accomplished by measuring the reaction diameters using an ocular micrometer. Since the shape of the tissue reaction tends to be elliptical, the formula for the area of an ellipse, $A = (D_1 \times D_2)/4 \times II$ is used to calculate these areas. The suture is included in these diameter measurements (See Tables 2 and 3).

The measurements of cellular invasion inside the silk braids are estimated subjectively as a percentage of suture area invaded.

DETERMINATION OF IN VIVO TENSILE STRENGTH LOSS

Breaking Strength Evaluation of Coated Silk Sutures After Implantation in Rats

The purpose of this study is to determine the breaking strength of silk sutures coated with a Polymer (P) coating (product of Example 2) at baseline (0 days), 7, 28 and 56 days in the rat subcutis.

Materials

Forty-eight young (approx. 200 gm) female Long-Evans (Blue Spruce Farms) rats.

Test Material

One lot each of sizes 2-0 and 5-0 sterile silk, coated as follows:

A. Standard Wax Coating
B. Polymer (P) Coating

Eight strands 18 inches each are used for each coating group.

Methods

Eight 18 inch strands of each coating type are divided into four groups of eight segments each. One segment from each of the strands is placed into each of three implanted groups (7, 28, 56 days) and one unimplanted (0 day) group. Each segment to be implanted is clamped at each end in a hemostatic forceps.

The rats are prepared for surgery by clipping fur from the dorsal scapular region of the skin. They are anesthetized using METOFANE* and swabbed in the operative area with an antiseptic solution.

A transverse incision approximately 2 cm. long is centered in the shaved area. Two segments of test material are implanted in the posterior dorsal subcutis through this single incision, one left and one right. The wound is closed with stainless steel wound clips.

Sutures are so implanted in four rats for each time period previously listed, thus yielding eight replicate segments/period.

The animals are sacrificed at the designated time periods and suture segments are gently and carefully removed from their respective sites. The recovered segments are stored in prelabeled moist paper towels for subsequent breaking strength testing.

All suture segments for this study are tested on an Instron Universal Testing Unit using the following machine parameters:

Jaw Face: Coplanar rubber faced steel
Gage Length: 1 inch
Crosshead distraction rate: 2 inches/minute Chart speed: 2 inches/minute
Jaw Pressure: 70 PSI
Baseline day sample condition: Dry

*Trademark of Pitman-Moore

Data Handling

The results of the breaking strength tests are summarized for each sample lot as follows:
Averages
Standard Deviation
95% upper and lower confidence limits
Conversion of all numbers to kilograms
Calculation of percent remaining of baseline These data are listed for each time period including baseline.

Results

Biological response, tensile strength loss and other physical test data are summarized in Tables 2, 3 and 4.

Discussion

The cellular responses to all the tested suture samples are foreign body in nature. However, the polymer (P) treated silk is extremely inert, provoking minimal to very slight tissue reaction scores and preventing cellular ingrowth inside the silk braid.

Oil Red 0 stained cross sections reveal that the polymer is infiltrated throughout the braid. In the case of the size 2-0 material, distribution of polymer tends to be higher in the peripheral carriers than in the central core. The extent of the polymer infiltration is similar after the 7, 28 and 56 day implantation periods, and comparable to the non-implanted suture cross sections.

The silk filaments of the polymer (P) treated samples have a less intense black coloration than the beeswaxed (control) silk filaments, but this can only be seen in the cross-sections and is not apparent grossly.

The waxed silk elicits a moderate tissue reaction. The primary cell types seen in these reaction zones are macrophages, multinucleated foreign body giant cells and fibro blasts. Individual filaments or bundles of filaments of the waxed silk sutures are separated and surrounded by inflammatory cells.

The cross-sectional areas of the waxed controls show considerable cell infiltration and consequent "explosions" of the silk braid.

After four and eight week implantation periods the polymer (P) treated silk exhibits increasingly greater strength retention compared with beeswaxed controls.

Infiltration of braided silk with the polymer (P) results in a tissue-inert silk suture with an excellent "silk hand" and an improved strength retention. Both tissue inertness and in vivo strength retention are rated significantly better than standard silk controls.

A further study, similar to the above is conducted utilizing 36 female Long Evans rats, rather than Sprague Dawley rats, and the results are summarized in Tables 5, 6, 7 and 8. Table 5 sets forth Average Breaking Strength values for polymer (P) coated Sutures after subcutaneous implantation in rats, whereas Tables 6, 7 and 8 relate to tissue response evaluation.

Results

The reactions elicited by the sutures are foreign body in nature. In implant sites of Polymer (P) sutures the reactions are primarily confined to the periphery of the suture. The reactions consist mostly of fibroblastic/fibrocytic cells and macrophages on the suture surface. Other inflammatory cells are absent or present in minimal numbers. Neutrophilic leukocytes are prominent in implant sites of wax coated sutures especially at seven days post implantation. Giant cell and fibroblast/fibrocyte cellular reaction are dominant in the 28 and 56 day waxed suture implant sites.

Fibrous encapsulation of Polymer (P) sutures is well-defined at 56 days while encapsulation of wax coated sutures is poorly defined at the interval.

With respect to overall reactions elicited by size 2-0 sutures, it is noted that Polymer (P) coated sutures tend to evoke less tissue reaction than wax coated silk at seven days post-implantation (see Table 6).

The areas of reaction zones for sizes 2-0 and 5-0 Polymer (P) coated sutures are significantly smaller than are observed for the control samples at 7, 28 and 56 days (see Table 7). The smaller tissue reaction areas observed for Polymer (P) coated sutures are due mainly to lesser amounts of interfibrillar cellular infiltration.

Polymer (P) coating is highly effective in preventing cellular invasion of both sizes of silk sutures at all three periods (7, 28 and 56 days) as shown in Table 8.

In hematoxylin and eosin stain sections of implant sites of paraffin/beeswax, coatings are not visible due to their solubility in histoprocessing solutions. Polymer (P) coating is faintly visible in ordinary transmitted light and is readily seen in polarized transmitted light. Sections of Polymer (P) coated suture sites stained with oil red 0 reveal the coating to be uniformly distributed at the periphery of the suture and variably dispersed around filaments near the center of the suture.

TABLE 2

Biological Response and Physical Test Data for Polymer (P) and Beeswax Paraffin Coated Sutures after Implantation in Sprague-Dawley Rats

| Size 2/0 | Period Days | Tissue Reaction Score $\bar{x}$ | $\sigma$ | Tissue Reaction Median & Range | | Cellular Invasion % $\bar{x}$ of % | $\sigma$ | Area of Suture & Tissue Reaction in Square mm. $\bar{x}$ | $\sigma$ | Tensile Strength in Kg. $\bar{x}$ | $\sigma$ | Strength Remaining % |
|---|---|---|---|---|---|---|---|---|---|---|---|---|
| Polymer (P) | 0 | — | — | — | — | — | — | — | — | 3.89 UCL 3.98 LCL 3.80 | 0.11 | 100.0 |
|  | 7 | 14.75 | 5.2 | 14 | (8–21) | 9.58 | 6.2 | .301 | .13 | 2.20 UCL 2.27 LCL 2.13 | .08 | 56.6 |
| Dry Day 0 T.S. $\bar{x}$ 3.89 kg. $\sigma$.11 | 28 | 10.75 | 3.0 | 10 | (5–18) | 5.00 | 5.2 | .215 | .04 | 1.92 UCL 2.02 LCL 1.82 | .12 | 49.4 |
| *UCL 3.98 LCL 3.80 | 56 | 10.58 | 3.7 | 10 | (5–17) | 2.92 | 7.2 | .183 | .03 | 1.55 UCL 1.65 LCL 1.45 | .12 | 39.9 |
| Beeswax Paraffin Control | 0 | — | — | — | — | — | — | — | — | 4.01 UCL 4.05 LCL 3.97 | .05 | 100.0 |
|  | 7 | 34.08 | 5.9 | 35.5 | (23–41) | 66.67 | 3.08 | .853 | .51 | 2.31 UCL 2.36 LCL 2.26 | .06 | 57.6 |
| Dry Day 0 T.S. $\bar{x}$ 4.01 kg. $\sigma$.05 | 28 | 33.42 | 1.8 | 33.5 | (31–36) | 100.00 | 0 | .448 | .11 | 1.52 UCL 1.69 LCL 1.35 | .20 | 37.9 |
| UCL 4.05 LCL 3.97 | 56 | 28.83 | 3.6 | 28.5 | (24–37) | 100.00 | 0 | .418 | .15 | 0.84 UCL 1.00 LCL .68 | .19 | 20.9 |

*UCL - 95% Upper Confidence Level
LCL - 95% Lower Confidence Level

TABLE 3

Biological Response and Physical Test Data for Polymer (P) and Beeswax Paraffin Coated Sutures after Implantation in Sprague Dawley Rats

| Size 5/0 | Period Days | Tissue Reaction Score $\bar{x}$ | $\sigma$ | Tissue Reaction Median & Range | | Cellular Invasion % $\bar{x}$ of % | $\sigma$ | Area of Suture & Tissue Reaction in Square mm. $\bar{x}$ | $\sigma$ | Tensile Strength in Kg. $\bar{x}$ | $\sigma$ | Strength Remaining % |
|---|---|---|---|---|---|---|---|---|---|---|---|---|
| Polymer (P) | 0 | — | — | — | — | — | — | — | — | 0.78 UCL .83 LCL .73 | .06 | 100.0 |
|  | 7 | 11.75 | 2.1 | 11 | (10–16) | 2.50 | 4.5 | .051 | .01 | .46 UCL .49 LCL .43 | .03 | 58.9 |
| Dry Day 0 T.S. $\bar{x}$ .78 kg. $\sigma$.06 | 28 | 10.90 | 1.5 | 10 | (10–13) | 3.18 | 4.1 | .040 | .01 | .36 UCL .39 LCL .33 | .03 | 46.2 |
| *UCL .83 LCL .73 | 56 | 11.58 | 1.8 | 11 | (10–15) | 1.67 | 2.5 | .043 | .01 | .25 UCL .27 LCL .23 | .03 | 32.1 |
| Beeswax Paraffin Control | 0 | — | — | — | — | — | — | — | — | .89 UCL .91 LCL .87 | .02 | 100.0 |
|  | 7 | 30.33 | 6.7 | 29 | (22–47) | 97.90 | 7.2 | .303 | .22 | .54 UCL .55 | .01 | 60.7 |

TABLE 3-continued

Biological Response and Physical Test Data for Polymer (P) and
Beeswax Paraffin Coated Sutures after Implantation in Sprague Dawley Rats

| Size 5/0 | Period Days | Tissue Reaction Score $\bar{x}$ | $\sigma$ | Tissue Reaction Median & Range | Cellular Invasion % $\bar{x}$ of % | $\sigma$ | Area of Suture & Tissue Reaction in Square mm. $\bar{x}$ | $\sigma$ | Tensile Strength in Kg. $\bar{x}$ | $\sigma$ | Strength Remaining % |
|---|---|---|---|---|---|---|---|---|---|---|---|
| Dry Day 0 T.S. $\bar{x}$ .89 kg. $\sigma$.02 | 28 | 21.00 | 3.3 | 20.5 (17–26) | 89.58 | 16.7 | .109 | .04 | LCL .53 .34 UCL .36 | .02 | 38.2 |
| UCL .91 LCL .87 | 56 | 21.50 | 4.0 | 20.0 (17–29) | 85.42 | 12.9 | .105 | .06 | LCL .32 .24 UCL .28 LCL .19 | .05 | 26.9 |

*UCL - 95% Upper Confidence Level
LCL - 95% Lower Confidence Level

TABLE 4

Physical Test Data for Non-Implanted Untreated Silk as
well as Polymer (P) and Beeswax Paraffin Coated Sutures

| | Dry Knot Pulls Kg. $\bar{x}$ | $\sigma$ | Straight Tensile Strength (kg) $\bar{x}$ | $\sigma$ | Diameter in mm. $\bar{x}$ | $\sigma$ |
|---|---|---|---|---|---|---|
| 2/0* | | | | | | |
| Polymer (P) | 2.18 | .13 | 3.89 | .11 | .340 | .013 |
| Beeswax Paraffin Control | 2.18 | .09 | 4.01 | .05 | .295 | .018 |
| Untreated Silk of Same Original Lot | 2.63 | .15 | 4.06 | .03 | .306 | .006 |
| 5/0* | | | | | | |
| Polymer (P) | .50 | .04 | .78 | .06 | .125 | .005 |
| Beeswax Paraffin Control | .52 | .04 | .89 | .02 | .127 | .005 |
| Untreated Silk of Same Original Lot | .56 | .04 | .78 | .10 | .130 | .003 |

*All measurements after CO Sterilization

TABLE 5

AVERAGE BREAKING STRENGTH VALUES
FOR POLYMER (P) SUTURES
AFTER SUBCUTANEOUS IMPLANTATION
IN LONG EVANS RATS
DATA EXPRESSED IN POUNDS

| | TIME IN DAYS | | | | |
|---|---|---|---|---|---|
| | 0 | 7 | 28 | 56 | DESCRIPTIONS |
| SIZE: 2-0 | 8.60 | 5.00 | 4.27 | 3.02 | PARAFFIN/ |
| % REMAINING | 100 | 58 | 50 | 35 | BEESWAX |
| SIZE: 2-0 | 8.31 | 5.13 | 4.37 | 3.88 | POLYMER (P) |
| % REMAINING | 100 | 62 | 53 | 47 | COATED |
| SIZE: 5-0 | 1.82 | 1.17 | 0.88 | 0.68 | PARAFFIN/ |
| % REMAINING | 100 | 64 | 49 | 37 | BEESWAX |
| SIZE: 5-0 | 1.65 | 0.99 | 0.79 | 0.74 | POLYMER (P) |
| % REMAINING | 100 | 60 | 48 | 45 | COATED |

TABLE 6

MEDIAN TISSUE OVERALL REACTION
SCORES FOR COATED
SILK SUTURES AFTER INTRAMUSCULAR
IMPLANTATION IN LONG EVANS RATS*

| SIZE | DESCRIPTION | DAYS POST-IMPLANTATION | | |
|---|---|---|---|---|
| | | 7 | 28 | 56 |
| 2-0 | Polymer (P) Coated | 14.5 (8–17) | 8 (6–14) | 11 (7–14) |
| 2-0 | Paraffin/Beeswax Coated | 38.5 (13–42) | 31 (17–52) | 25.5 (15–40) |
| 5-0 | Polymer (P) Coated | 16 (13–23) | 7.5 (5–15) | 10.5 (8–14) |
| 5-0 | Paraffin/Beeswax Coated | 26 (20–30) | 17 (14–34) | 16 (15–23) |

*Data represent the median of 10–12 cross section in three rats per period. Arbitrary assignment of scores are as follows: 1–8 minimal, 9–24 slight, 25–40 moderate, 41–56 marked, 56+ extensive.
** ( ) = range of tissue reaction scores for the period.

TABLE 7

AVERAGE TISSUE REACTION AREAS
FOR COATED SILK SUTURES
AFTER INTRAMUSCULAR IMPLANTATION
IN LONG EVANS RATS*

| SIZE | DESCRIPTION | DAYS POST-IMPLANTATION | | |
|---|---|---|---|---|
| | | 7 | 28 | 56 |
| 2-0 | Polymer (P) Coated | .204 (.026) | .196 (.026) | .170 (.030) |
| 2-0 | Paraffin/Beeswax Coated | .857 (.200) | .768 (.415) | .539 (.331) |
| 5-0 | Polymer (P) Coated | .112 (.036) | .049 (.009) | .053 (.013) |
| 5-0 | Paraffin/Beeswax Coated | .280 (.074) | .161 (.040) | .143 (.041) |

*Data represent the mean of 10–12 cross sections per period and are presented in square millimeters ($mm^2$).
**( ) = Standard deviation.

TABLE 8

DEGREE OF INTERFIBRILLAR CELLULAR
INFILTRATION INTO
COATED SILK SUTURES AFTER
INTRAMUSCULAR IMPLANTATION
IN LONG EVANS RATS*

| SIZE | DESCRIPTION | DAYS POST-IMPLANTATION | | |
|---|---|---|---|---|
| | | 7 | 28 | 56 |
| 2-0 | Polymer (P) Coated | 0.6** | 0.7 | 0.9 |
| 2-0 | Paraffin/Beeswax Coated | 4.0 | 3.8 | 3.8 |
| 5-0 | Polymer (P) Coated | 0.5 | 0.7 | 0.8 |
| 5-0 | Paraffin/Beeswax Coated | 3.9 | 3.9 | 4.0 |

*Data represent the average of 10–12 cross sections per period.
**Arbitrary assignment of scores is as follows:
0 = no infiltration
1 = slight infiltration
2 = moderate infiltration
3 = marked infiltration
4 = complete infiltration

EXAMPLE 1

Polymer (P) Poly[tetramethylene terephthalate-Co-Poly(oxytetramethylene terephthalate)](25/75 PBT/POTM-T)

Under a dry nitrogen atmosphere, the following materials are placed into a flame and vacuum dried 300 ml two-neck, round-bottom flask equipped with a stainless steel paddle stirrer, a short distilling head fitting with a receiver, and a gas inlet nozzle:

| 27.9 g 1,4 dimethyl terephthalate | (0.1439 mol) |
| 24.6 g 1,4 butanediol | (0.2730 mol) |
| 53.1 g (Poly tetramethylene oxide diol). (Molecular Weight 1000 Dalton) | (0.0531 mol) |
| 0.16 g Irganox 1098 | |

After stoppering the open neck of the flask, the entire charge-containing assembly is removed from the nitrogen atmosphere and exposed to a high (less than 1 mm) vacuum for several hours. The charged reaction vessel is then vented with nitrogen, and the reactants are melted by heating to 165° C. Once the charge is liquified, the reaction flask is connected to an efficient mechanical stirrer and thorough mixing at 165° C. is performed for 15 minutes. Next, the catalyst consisting of a mixture of tetrabutyl orthotitante (0.244 g) and magnesium acetate (0.01 g) dissolved in a mixture of methanol and butanol, is quickly syringed into the reaction vessel via the side arm. Still under a continuous flow of nitrogen, the melted reaction mixture is then subjected to the following heating sequence: 190° C. for 2.5 hours, 220° C. for 2.5 hours.

As the distillation of volatile by-products slows, after 2.5 hours at 220° C., the receiver containing the distillate is replaced with an empty receiver. Then, gradually over the course of 0.75 hours the pressure in the reaction flask is reduced to 0.05 mm. Under reduced pressure the reaction mixture is subjected to the following heating scheme: 230° C. for 4.5 hours.

At the end of this heating cycle, the reaction vessel is removed from the oil bath, equilibrated with nitrogen, and then allowed to cool to room temperature. The polymer is isolated after chilling in liquid nitrogen, ground, and then dried under vacuum.

EXAMPLE 2

Polymer (P) Poly[tetramethylene terephthalate-Co-Poly-(oxytetramethylene terephthalate)](29/71 PBT/POTM-T)

Under a dry nitrogen atmosphere, the following materials are placed into a flame and vacuum dried 500 ml two-neck, round-bottom flask equipped with a stainless steel paddle stirrer, a short distilling head fitting with a receiver, and a gas inlet nozzle:

| 38.8 g 1,4 dimethyl terephthalate | (0.1998 mol) |
| 37.7 g 1,4 butanediol | (0.4183 mol) |
| 65.4 g (Poly tetramethylene oxide diol) Molecular Weight 1000 Dalton | (0.0654 mol) |
| 0.0331 g dibutyl tin oxide | (0.000133 mol) |

After stoppering the open neck of the flask, the entire charge-containing assembly is removed from the nitrogen atmosphere and exposed to a high (less than 1 mm) vacuum for several hours. The charged reaction vessel is then vented with nitrogen, and the reactants are melted by heating to 165° C. Once the charge is liquified, the reaction flask is connected to an efficient mechanical stirrer and thorough mixing at 165° C. is performed for 15 minutes. Still under a continuous flow of nitrogen, the melted reaction mixture is then subjected to the following heating sequence: 190° C. for 3.0 hours, 230° C. for 4.0 hours.

As the distillation of volatile by-products slows, after 4.0 hours at 230° C., the receiver containing the distillate is replaced with an empty receiver. Then, gradually over the course of 0.75 hours the pressure in the reaction flask is reduced to 0.05 mm. Under reduced pressure the reaction mixture is subjected to the following heating scheme: 230° C. for 6.0 hours.

At the end of this heating cycle, the reaction vessel is removed from the oil bath, equilibrated with nitrogen, and then allowed to cool to room temperature. The polymer is isolated after chilling in liquid nitrogen, ground, and then dried under vacuum.

| Analytical Data: | Tm (microscopy) 140°–150° C. |
| | I.V. (in HFIP) 1.2 |

EXAMPLE 3

Polymer (P) Poly[tetramethylene terephthalate-Co-Poly(oxytetramethylene terephthalate)](45/55 PBT/POTM-T)

Under a dry nitrogen atmosphere, the following materials are placed into a flame and vacuum dried 300 ml two-neck, round-bottom flask equipped with a stainless steel paddle stirrer, a short distilling head fitting with a receiver, and a gas inlet nozzle:

| 39.3 g 1,4 dimethyl terephthalate | (0.2024 mol) |
| 44.1 g 1,4 butanediol | (0.4893 mol) |
| 38.9 g (Poly tetramethylene oxide diol) Molecular Weight 1000 Dalton | (0.0389 mol) |
| 0.16 g Irganox 1098 | |

After stoppering the open neck of the flask, the entire charge-containing assembly is removed from the nitrogen atmosphere and exposed to a high (less than 1 mm) vacuum for several hours. The charged reaction vessel is then vented with nitrogen, and the reactants are melted by heating to 165° C. Once the charge is liquified, the reaction flask is connected to an efficient mechanical stirrer and thorough mixing at 165° C. is performed for 15 minutes. Next, the catalyst consisting of a mixture of tetrabutyl orthotitanate (0.244 g) and magnesium acetate (0.01 g) dissolved in a mixture of methanol and butanol, is quickly syringed into the reaction vessel via the side arm. Still under a continuous flow of nitrogen, the melted reaction mixture is then subjected to the following heating sequence: 190° C. for 2.0 hours, 220° C. for 2.5 hours.

As the distillation of volatile by-products slows, after 2.5 hours at 220° C., the receiver containing the distillate is replaced with an empty receiver. Then, gradually over the course of 0.75 hours the pressure in the reaction flask is reduced to 0.05 mm. Under reduced pressure the reaction mixture is subjected to the following heating scheme: 230° C. for 3.5 hours.

At the end of this heating cycle, the reaction vessel is removed from the oil bath, equilibrated with nitrogen, and then allowed to cool to room temperature. The polymer is isolated after chilling in liquid nitrogen, ground, and then dried under vacuum.

EXAMPLE 4

Polymer (R) Poly[tetramethylene terephthalate-Co-(2-octadecenyl)succinate](40/60 PBT/C$_{18}$succinate)

Under a dry nitrogen atmosphere, the following materials are placed into a flame and vacuum dried 300 ml two-neck, round-bottom flask equipped with a stainless steel paddle stirrer, a short distilling head fitting with a receiver, and a gas inlet nozzle:

| | |
|---|---|
| 28.2 g 1,4 dimethyl terephthalate | (0.1453 mol) |
| 39.8 g 2-octadecenyl succinic anhydride | (0.1136 mol) |
| 69.9 g 1,4 butanediol | (0.7756 mol) |
| 0.16 g Irganox 1098 | |

After stoppering the open neck of the flask, the entire charge-containing assembly is removed from the nitrogen atmosphere and exposed to a high (less than 1 mm) vacuum for several hours. The charged reaction vessel is then vented with nitrogen, and the reactants are melted by heating to 165° C. Once the charge is liquified, the reaction flask is connected to an efficient mechanical stirrer and thorough mixing at 165° C. is performed for 15 minutes. Next, the catalyst consisting of a mixture of tetrabutyl orthotitanate (0.244 g) and magnesium acetate (0.01 g) dissolved in a mixture of methanol and butanol, is quickly syringed into the reaction vessel via the side arm. Still under a continuous flow of nitrogen, the melted reaction mixture is then subjected to the following heating sequence: 190° C. for 3.0 hours, 220° C. for 3.0 hours.

As the distillation of volatile by-products slows, after 3.0 hours at 220° C., the receiver containing the distillate is replaced with an empty receiver. Then, gradually over the course of 0.75 hours the pressure in the reaction flask is reduced to 0.05 mm. Under reduced pressure the reaction mixture is subjected to the following heating scheme: 240° C. for 2.0 hours, 250° C. for 2.0 hours.

At the end of this heating cycle, the reaction vessel is removed from the oil bath, equilibrated with nitrogen, and then allowed to cool to room temperature. The polymer is isolated after chilling in liquid nitrogen, ground, and then dried under vacuum.

| | |
|---|---|
| Analytical Data: | Tm (microscopy) 113°–118° C. |
| | I.V. (in HFIP) 0.46 |

EXAMPLE 5

Polymer (S) Poly[poly(tetramethylene oxybenzoate)-Co-poly(hexamethylene-2-octadecenyl succinate)](40/60 PBB/C$_{18}$succinate)

Under a dry nitrogen atmosphere, the following materials are placed into a flame and vacuum dried 300 ml two-neck, round-bottom flask equipped with a stainless steel paddle stirrer, a short distilling head fitting with a receiver, and a gas inlet nozzle:

| | |
|---|---|
| 37.3 g methyl para(4-hydroxy butoxy)benzoate | (0.1666 mol) |
| 37.3 g 2-octadecenyl succinic anhydride | (0.1065 mol) |
| 13.9 g 1,6 hexanediol | (0.1176 mol) |
| 0.16 g Irganox 1098 | |

After stoppering the open neck of the flask, the entire charge-containing assembly is removed from the nitrogen atmosphere and exposed to a high (less than 1 mm) vacuum for several hours. The charged reaction vessel is then vented with nitrogen, and the reactants are melted by heating to 100° C. Once the charge is liquified, the reaction flask is connected to an efficient mechanical stirrer and thorough mixing at 100° C. is performed for 15 minutes. Next, the catalyst consisting of a mixture of tetrabutyl orthotitanate (0.305 g) and magnesium acetate (0.0125 g) dissolved in a mixture of methanol and butanol, is quickly syringed into the reaction vessel via the side arm. Still under a continuous flow of nitrogen, the melted reaction mixture is then subjected to the following heating sequence: 190° C. for 2.5 hours, 220° C. for 3.0 hours, 240° C. for 2.25 hours.

As the distillation of volatile by-products slows, after 2.25 hours at 240° C., the receiver containing the distillate is replaced with an empty receiver. Then, gradually over the course of 0.75 hours the pressure in the reaction flask is reduced to 0.05 mm. Under reduced pressure the reaction mixture is subjected to the following heating scheme: 240° C. for 2.5 hours, 250° C. for 2.75 hours.

At the end of this heating cycle, the reaction vessel is removed from the oil bath, equilibrated with nitrogen, and then allowed to cool to room temperature. The polymer is isolated after chilling in liquid nitrogen, ground, and then dried under vacuum.

Analytical Data: Tm(microscopy) 50°–70° C.

EXAMPLE 6

Polymer (S) Poly[poly(tetramethylene oxybenzoate)-Co-poly(hexamethylene-2-octadecenyl succinate)](50/50 PBB/C$_{18}$succinate)

Under a dry nitrogen atmosphere, the following materials are placed into a flame and vacuum dried 300 ml two-neck, round-bottom flask equipped with a stainless steel paddle stirrer, a short distilling head fitting with a receiver, and a gas inlet nozzle:

| | |
|---|---|
| 46.7 g methyl para(4-hydroxy butoxy)benzoate | (0.2082 mol) |
| 31.1 g 2-octadecenyl succinic anhydride | (0.0888 mol) |
| 11.6 g 1,6 hexanediol | (0.0981 mol) |
| 0.16 g Irganox 1098 | |

After stoppering the open neck of the flask, the entire charge-containing assembly is removed from the nitrogen atmosphere and exposed to a high (less than 1 mm) vacuum for several hours. The charged reaction vessel is then vented with nitrogen, and the reactants are melted by heating to 100° C. Once the charge is liquified, the reaction flask is connected to an efficient mechanical stirrer and thorough mixing at 100° C. is performed for 15 minutes. Next, the catalyst consisting of a mixture of tetrabutyl orthotitanate (0.305 g) and magnesium acetate (0.0125 g) dissolved in a mixture of methanol and butanol, is quickly syringed into the reaction vessel via the side arm. Still under a continuous flow of nitrogen, the melted reaction mixture is then subjected to the following heating sequence: 190° C. for 3.0 hours, 220° C. for 2.3 hours, and 240° C. for 1.25 hours.

As the distillation of volatile by-products slows, after 1.25 hours at 240° C., the receiver containing the distillate is replaced with an empty receiver. Then, gradually over the course of 0.75 hours the pressure in the reaction flask is reduced to 0.05 mm. Under reduced pressure the reaction mixture is subjected to the following heating scheme: 240° C. for 4.5 hours.

At the end of this heating cycle, the reaction vessel is removed from the oil bath, equilibrated with nitrogen, and then allowed to cool to room temperature. The polymer is isolated after chilling in liquid nitrogen, ground, and then dried under vacuum.

| Analytical Data: | Tm (microscopy) 98°–101° C. |
| --- | --- |
| | I.V. (in HFIP) 0.38 |

EXAMPLE 7

Polymer (Q) Poly[tetramethylene terephthalate-Co-dimerate](30/70 PBT/dimerate)

Under a dry nitrogen atmosphere, the following materials are placed into a flame and vacuum dried 300 ml two-neck, round-bottom flask equipped with a stainless steel paddle stirrer, a short distilling head fitting with a receiver, and a gas inlet nozzle:

| 21.2 g 1,4 dimethyl terephthalate | (0.1090 mol) |
| --- | --- |
| 58.7 g diisopropyl dimerate | (0.0903 mol) |
| 53.7 g 1,4 butanediol | (0.5959 mol) |
| 0.16 g Irganox 1098 | |

After stoppering the open neck of the flask, the entire charge-containing assembly is removed from the nitrogen atmosphere and exposed to a high (less than 1 mm) vacuum for several hours. The charged reaction vessel is then vented with nitrogen, and the reactants are melted by heating to 165° C. Once the charge is liquified, the reaction flask is connected to an efficient mechanical stirrer and thorough mixing at 165° C. is performed for 15 minutes. Next, the catalyst consisting of a mixture of tetrabutyl orthotitanate (0.244 g) and magnesium acetate (0.01 g) dissolved in a mixture of methanol and butanol, is quickly syringed into the reaction vessel via the side arm. Still under a continuous flow of nitrogen, the melted reaction mixture is then subjected to the following heating sequence: 190° C. for 2.0 hours, 220° C. for 2.5 hours.

As the distillation of volatile by-products slows, after 2.5 hours at 220° C., the receiver containing the distillate is replaced with an empty receiver. Then, gradually over the course of 0.75 hours the pressure in the reaction flask is reduced to 0.05 mm. Under reduced pressure the reaction mixture is subjected to the following heating scheme: 240° C. for 3.5 hours.

At the end of this heating cycle, the reaction vessel is removed from the oil bath, equilibrated with nitrogen, and then allowed to cool to room temperature. The polymer is isolated after chilling in liquid nitrogen, ground, and then dried under vacuum.

| Analytical Data: | Tm (microscopy) 151°–156° C. |
| --- | --- |
| | I.V. (in HFIP) 0.36 |

EXAMPLE 8

Polymer (Q) Poly[tetramethylene terephthalate-Co-dimerate](40/60 PBT/dimerate)

Under a dry nitrogen atmosphere, the following materials are placed into a flame and vacuum dried 300 ml two-neck, round-bottom flask equipped with a stainless steel paddle stirrer, a short distilling head fitting with a receiver, and a gas inlet nozzle:

| 28.2 g 1,4 dimethyl terephthalate | (0.1453 mol) |
| --- | --- |
| 50.3 g diisopropyl dimerate | (0.0774 mol) |
| 60.3 g 1,4 butanediol | (0.6691 mol) |
| 0.16 g Irganox 1098 | |

After stoppering the open neck of the flask, the entire charge-containing assembly is removed from the nitrogen atmosphere and exposed to a high (less than 1 mm) vacuum for several hours. The charged reaction vessel is then vented with nitrogen, and the reactants are melted by heating to 165° C. Once the charge is liquified, the reaction flask is connected to an efficient mechanical stirrer and thorough mixing at 165° C. is performed for 15 minutes. Next, the catalyst consisting of a mixture of tetrabutyl orthotitanate (0.244 g) and magnesium acetate (0.01 g) dissolved in a mixture of methanol and butanol, is quickly syringed into the reaction vessel via the side arm. Still under a continuous flow of nitrogen, the melted reaction mixture is then subjected to the following heating sequence: 190° C. for 2.5 hours, 220° C. for 3.0 hours.

As the distillation of volatile by-products slows, after 3.0 hours at 220° C., the receiver containing the distillate is replaced with an empty receiver. Then, gradually over the course of 0.75 hours the pressure in the reaction flask is reduced to 0.05 mm. Under reduced pressure the reaction mixture is subjected to the following heating scheme: 240° C. for 2.0 hours.

At the end of this heating cycle, the reaction vessel is removed from the oil bath, equilibrated with nitrogen, and then allowed to cool to room temperature. The polymer is isolated after chilling in liquid nitrogen, ground, and then dried under vacuum.

| Analytical Data: | Tm (microscopy) 148°–151° C. |
| --- | --- |
| | I.V. (in HFIP) 0.23 |

EXAMPLE 9

Impregnation of Silk Suture with Polymer

The laboratory coating line consists of the conventional spool let-off, solution treatment, drying the suture takeup operations, arranged sequentially. Two black dyed silk sutures, sizes 2-0 and 5-0 are treated. The suture material is passed through a 15–20% w/v solution of polymer (P) prepared in accordance with Example 2 in dichlormethane, maintained at 40°±5° C.

On emerging from the polymer solution, excess solution is removed by passage through a felt wipe. Solvent is evaporated by running the sutures past a hot air blower (150° C.).

Both polymer solution temperature and concentration are important in achieving the desired polymer add-on in a single pass. Desirable polymer add-on is in the 7–15% range, with a value of 9% for size 2-0 and 12% for size 5-0.

At this stage of the process, the polymer encapsulates the suture and does not appreciably penetrate the interior of the braid. The hand of this material is very stiff. Desirable suture properties of hand and knot-tying are achieved by causing the polymer to infiltrate and penetrate the interior of the braid by subjecting the polymer sheathed suture to a short duration, high temperature heating stage.

The polymer sheathed suture is passed in a vertical mode centrally through a 0.5 cm diameter hole bored in a 22 cm electrically heated aluminum block. Conditions of block temperature and suture speed for achieving optimum infiltration are given below:

| Suture Size | Block Temperature | Suture Speed |
| --- | --- | --- |
| 2–0 | 415 ± 5° C. | 7.1 cm/sec |
| 5–0 | 345 ± 5° C. | 9.6 cm/sec |

The above conditions are found to confer a soft, supple hand, as contrasted to the stiff, wiry hand of the encapsulated suture.

We claim:

1. A composite suture essentially retaining the handling qualities of silk, which, in the case of size 5–0, is capable of retaining at least 32% of its initial mechanical strength, in vivo, after eight weeks; said suture having surface barrier properties against cell infiltration comparable to those of a monofilament and tissue reaction comparable to common synthetic sutures; comprising multifilament silk embedded in a hydrophobic, limp thermoplastic elastomer, substantially all the interstices between the silk filaments being filled by said elastomer; said elastomer having a suitable molecular weight sufficient to provide a solution viscosity that is consistent with optimum diffusion into the interior of the suture structure, resulting in a high integrity matrix which does not flake when the suture is subjected to mechanical stress; said elastomer being selected from the group consisting of copolymers having the following recurring units:

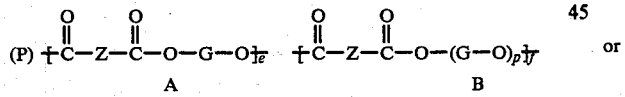

wherein each G individually represents an alkylene group of from 2 to 6 carbon atoms, and p is 9 to 15, e and f each represent a number having a value greater than 1 such that the B units comprise 50 to 80 weight percent of the copolymer and the A units comprise the remainder; wherein Z represents 1,4-phenylene, 1,3-phenylene or trans-1,4-cyclohexylene;

(Q) a copolymer consisting essentially of a multiplicity of recurring A [poly(alkylene terephthalate, isophthalate or cyclohexane-1,4-dicarboxylate)] and B [poly(alkylene dimerate)] units having the following general formula:

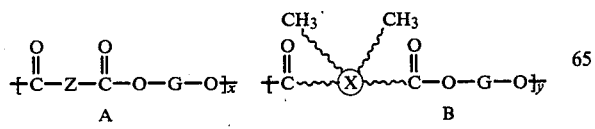

wherein x and y are integers, such that the B units comprise 50 to 80 weight percent of the copolymer, and the A units comprise the remainder;

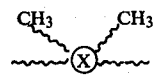

denotes a branched hydrocarbon chain containing from 24 to 32 carbon atoms and Z and G are as hereinabove defined;

(R) a copolymer consisting essentially of a multiplicity of recurring poly(alkylene) terephthalate, isophthalate or cyclohexane-1,4-dicarboxylate, and poly(alkylene) alkyl or alkenyl succinate units having the following general formula:

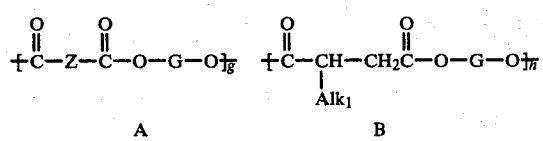

wherein $Alk_1$ is a linear or branched alkyl or alkenyl radical with a chain length of about 4 to 30 carbon atoms and g and h are integers such that the A units comprise 20 to 50 weight percent of the copolymer and the B units comprise the remainder and Z and G are as hereinabove defined; or, (S) a random copolymer having the following general formula:

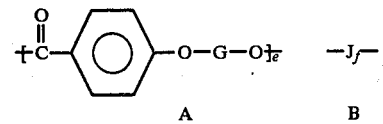

wherein J is either:

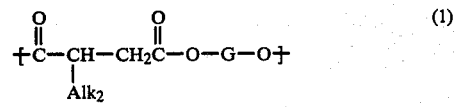

(1)

wherein $Alk_2$ is alkyl or alkenyl moieties with a chain length of 8 to 30 carbon atoms;

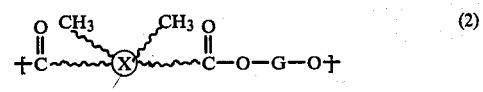

(2)

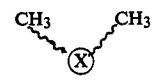

denotes a branched hydrocarbon chain with an estimated formula of $C_{32}H_{60}$, or

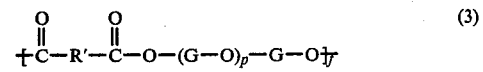

(3)

wherein p is 9 to 15, G is an hereinabove defined and R' is an aliphatic or aromatic disubstituted moiety and wherein e and f are such that the B units comprise about 25 to 50% by weight of the copolyester and the A units comprise the remainder.

2. A composite suture, comprising multifilament silk embedded in a hydrophobic, limp thermoplastic elastomer, said elastomer being selected from the group consisting of copolymers having the following recurring units:

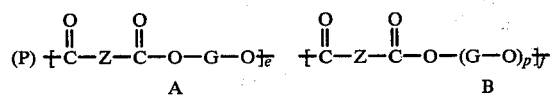

wherein each G individually represents an alkylene group of from 2 to 6 carbon atoms, and p is 9 to 15, e and f each represent a number having a value greater than 1 such that the B units comprise 50 to 80 weight percent of the copolymer and the A units comprise the remainder; wherein Z represents 1,4-phenylene, 1,3-phenylene or trans-1,4-cyclohexylene;

(Q) a copolymer consisting essentially of a multiplicity of recurring A [poly(alkylene terephthalate, isophthalate or cyclohexane-1,4-dicarboxylate)] and B [poly(alkylene dimerate)] units having the following general formula:

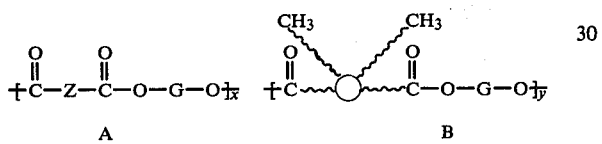

wherein x and y are integers, such that the B units comprise 50 to 80 weight percent of the copolymer, and the A units comprise the remainder;

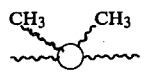

denotes a branched hydrocarbon chain containing from 24 to 32 carbon atoms and Z and G are as hereinabove defined;

(R) a copolymer consisting essentially of a multiplicity of recurring poly(alkylene) terephthalate, isophthalate or cyclohexane-1,4-dicarboxylate, and poly(alkylene) alkyl or alkenyl succinate units having the following general formula:

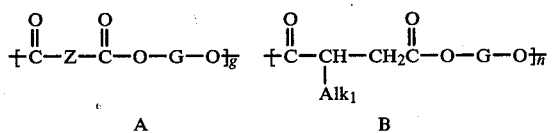

wherein $Alk_1$ is a linear or branched alkyl or alkenyl radical with a chain length of about 4 to 30 carbon atoms and g and h are integers such that the A units comprise 20 to 50 weight percent of the copolymer and the B units comprise the remainder and Z and G are as hereinabove defined; or, (S) a random copolymer having the following general formula:

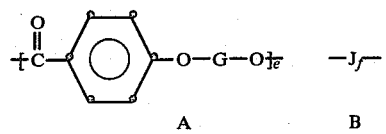

wherein J is either:

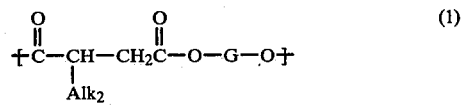

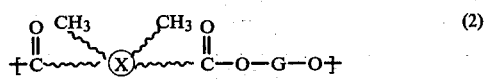

wherein $Alk_2$ is alkyl or alkenyl moieties with a chain length of 8 to 30 carbon atoms;

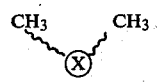

denotes a branched hydrocarbon chain with an estimated formula of $C_{32}H_{60}$, or

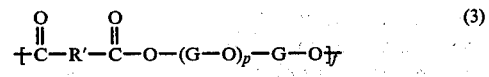

wherein p is 9 to 15, G is as hereinabove defined and R' is an aliphatic or aromatic disubstituted moiety and wherein e and f are such that the B units comprise about 25 to 50% by weight of the copolyester and the A units comprise the remainder.

3. A suture according to claim 2 or 1 wherein Z is 1,4-phenylene, G is 1,4 butylene, and the elastomer has an inherent viscosity of between 0.2 and 1.4 and has a melting temperature, by thermal microscopy of between about 80° and 180° C.

4. A suture according to claim 3 wherein the elastomer comprises 5–50% by weight of the total composite system and has a molecular weight of at least 2000 Dalton.

5. A suture according to claim 3 wherein the elastomer has the formula (P), (Q) or (R) and the B units comprise between 55% and 75% thereof.

6. A suture according to claim 5 wherein the B units of the elastomer comprise between 60% and 70% by weight thereof.

7. A suture according to claim 3 wherein the elastomer has the formula (S) and the B units comprise between 30% and 50% thereof.

8. A suture according to claim 3 wherein the elastomer has the formula (P) and the inherent viscosity in hexafluoro-2-propanol is between 0.8 and 1.3.

9. A suture according to claim 3 wherein the polymer has the formula (Q) and the inherent viscosity in hexafluoro-2-propanol is between 0.3 and 0.9.

10. A suture according to claim 3 wherein the polymer has the formula (R) and the inherent viscosity in hexafluoro-2-propanol is between 0.2 and 0.7.

11. A suture according to claim 3 wherein the polymer has the formula (S) and the inherent viscosity in hexafluoro-2-propanol is between 0.3 and 0.6.

12. A suture according to claim 1 wherein the silk is of braided construction.

13. A suture according to claim 1 having a surgical needle attached to at least one end.

14. A suture according to claim 13 or 1 in a sterile condition.

* * * * *